United States Patent
Vargas

(10) Patent No.: US 11,957,808 B2
(45) Date of Patent: Apr. 16, 2024

(54) FACE MASK TREE

(71) Applicant: Kathy Vargas, Bonita, CA (US)

(72) Inventor: Kathy Vargas, Bonita, CA (US)

(*) Notice: Subject to any disclaimer, the term of this patent is extended or adjusted under 35 U.S.C. 154(b) by 439 days.

(21) Appl. No.: 17/232,250

(22) Filed: Apr. 16, 2021

(65) Prior Publication Data
US 2022/0175998 A1    Jun. 9, 2022

Related U.S. Application Data

(60) Provisional application No. 63/123,143, filed on Dec. 9, 2020.

(51) Int. Cl.
| | |
|---|---|
| *A61L 2/26* | (2006.01) |
| *A47B 49/00* | (2006.01) |
| *A47G 25/10* | (2006.01) |
| *A47G 25/14* | (2006.01) |
| *A61L 2/10* | (2006.01) |
| *A61L 2/18* | (2006.01) |

(52) U.S. Cl.
CPC .............. *A61L 2/26* (2013.01); *A47B 49/008* (2013.01); *A47G 25/10* (2013.01); *A47G 25/14* (2013.01); *A61L 2/10* (2013.01); *A61L 2/186* (2013.01); *A61L 2202/11* (2013.01); *A61L 2202/15* (2013.01); *A61L 2202/24* (2013.01); *A61L 2202/26* (2013.01)

(58) Field of Classification Search
CPC ... A61L 2/10; A61L 2/26; A61L 2/186; A61L 2202/11; A61L 2202/15; A61L 2202/24; A61L 2202/26; A47G 25/10; A47G 25/14; A47B 49/008
See application file for complete search history.

(56) References Cited

U.S. PATENT DOCUMENTS

| | | | | | |
|---|---|---|---|---|---|
| 2,010,093 | A | * | 8/1935 | Lazarus | A47G 25/10 |
| | | | | | 33/8 |
| 3,421,762 | A | * | 1/1969 | Paradise | A63F 9/0208 |
| | | | | | 211/208 |
| 5,160,699 | A | * | 11/1992 | Siegal | A61L 2/10 |
| | | | | | 250/455.11 |
| 5,848,710 | A | * | 12/1998 | Pomper | A47F 7/024 |
| | | | | | 211/85.2 |
| 7,451,882 | B2 | * | 11/2008 | McKay | A47F 5/02 |
| | | | | | 211/85.2 |
| D610,370 | S | * | 2/2010 | Quan | D6/681.3 |

(Continued)

FOREIGN PATENT DOCUMENTS

| | | | | |
|---|---|---|---|---|
| DE | 102020115532 A1 | * | 12/2020 | ............... A61L 2/10 |
| DE | 202020101646 U1 | * | 8/2021 | ............... A61L 2/10 |
| WO | WO-2022076201 A1 | * | 4/2022 | |

*Primary Examiner* — Patrick D Hawn
(74) *Attorney, Agent, or Firm* — Brennan, Manna & Diamond, LLC

(57) ABSTRACT

This present invention relates to a mask or PPE storage device for storing protective face masks and other personal protective equipment, while helping to keep the stored face masks clean and hygienic for use. The mask storage device is a tree shaped stand and has a pole attached to a base, with several pegs or extenders attached to the pole. The pegs enable the users to easily hang their protective face mask or other accessories from the pegs. The mask storage stand offers a convenient and sanitary way to store masks while eating or drinking at bars, restaurants, schools, churches, or other similar places.

11 Claims, 3 Drawing Sheets

(56) References Cited

U.S. PATENT DOCUMENTS

| | | | | |
|---|---|---|---|---|
| 7,891,506 | B2* | 2/2011 | Kornowski | A47F 7/02 |
| | | | | 211/85.2 |
| 8,074,815 | B2* | 12/2011 | Gerstner | A61B 50/13 |
| | | | | 108/115 |
| 9,107,514 | B1* | 8/2015 | Morieras | A47F 7/02 |
| 10,219,605 | B1* | 3/2019 | Love | A47F 5/04 |
| 11,351,281 | B2* | 6/2022 | Gutterman | A61L 2/07 |
| 11,596,703 | B2* | 3/2023 | Farrell | A47B 49/004 |
| 11,672,880 | B2* | 6/2023 | Bohnert | A61L 2/208 |
| | | | | 422/28 |
| 11,712,492 | B2* | 8/2023 | Ketels | A61L 2/10 |
| | | | | 422/302 |
| 2003/0192840 | A1* | 10/2003 | Hoyle | A47F 7/02 |
| | | | | 211/85.2 |
| 2011/0089127 | A1* | 4/2011 | Thomas | A47F 5/02 |
| | | | | 211/183 |
| 2013/0168342 | A1* | 7/2013 | Yatscoff | A47F 5/04 |
| | | | | 211/85.2 |
| 2016/0324997 | A1* | 11/2016 | Dayton | A61L 2/10 |
| 2021/0299304 | A1* | 9/2021 | Concannon | A61L 2/26 |
| 2021/0299311 | A1* | 9/2021 | Yu | B08B 13/00 |
| 2021/0322591 | A1* | 10/2021 | Kirschner | A45D 44/04 |
| 2022/0062482 | A1* | 3/2022 | Farrell | A61L 2/10 |
| 2022/0098730 | A1* | 3/2022 | Mane | C23C 16/40 |
| 2022/0313849 | A1* | 10/2022 | Robinson | A47B 49/004 |

* cited by examiner

FACE MASK TREE

CROSS-REFERENCE TO RELATED APPLICATION

The present application claims priority to, and the benefit of, U.S. Provisional Application No. 63/123,143, which was filed on Dec. 9, 2020 and is incorporated herein by reference in its entirety.

FIELD OF THE INVENTION

The present invention relates generally to the field of personal care accessories. More specifically, the present invention relates to a rack or support such as a "tree" for supporting and sanitizing face masks and other personal protection equipment (PPE). The mask tree or PPE support includes several pegs or extenders attached to a central supporting pole that enable a user to hang various masks by their straps or ear loops over the pegs. The central supporting pole is attached to a flat base stand, which enables the mask support or tree to be placed on a table or another desired surface. The face mask tree offers an easy way of storing and sanitizing face masks or other PPE in homes, bars, restaurants, schools and many other locations, while also preventing the masks from becoming contaminated or unsanitary if brought into contact with an unclean surface. Accordingly, the present disclosure makes specific reference thereto. Nonetheless, it is to be appreciated that aspects of the present invention are also equally applicable to other like applications, devices and methods of manufacture.

BACKGROUND OF THE INVENTION

By way of background, people around the world use various devices or accessories to protect themselves from pandemics or other infectious diseases. A pandemic is an epidemic of an infectious disease that spreads across a large region, thereby affecting a substantial number of people. Various infectious diseases are spread through the transmission of harmful pathogens, such as viruses, bacteria, germs, pathogens, microbes or the like. Individuals coming in contact with an infected individual or surface can become quickly infected, and may suffer from the infectious diseases and other illness. In certain situations, such as the current COVID-19 pandemic, the rapid spread of the infectious disease may result in a significant number of deaths.

To prevent the transmission of infection diseases and other harmful pathogens, various precautionary guidelines have been promulgated and are oftentimes mandated by the authorities. For example, during the ongoing COVID-19 pandemic, individuals have been advised, and in some circumstances mandated, to frequently sanitize their hands and wear face masks while in public areas, or when away from home. Protective face masks act as barriers between the oral and nasal passageways of individuals and the environment, and help to prevent the transmission of harmful pathogens, viruses and bacteria from the environment to the individual wearing the face mask and vice versa. Additionally, such face masks may also be routinely worn by individuals suffering from a respiratory illness.

When a protective face mask is not required to be worn, many individuals will take their mask off and may place it in a pocket, or on a table or other surface, etc. until the same is needed again. Unfortunately, such surfaces and temporary storage places may be unsanitary, which can contaminate the mask and lead to the further spread of infectious diseases or harmful pathogens. Additionally, when a face mask is kept in a pocket or purse, there may be a risk of the mask falling on the floor, which can also result in the mask becoming contaminated or lost if the owner of the mask is unaware that the mask has fallen out of their pocket or purse. A dirty, unsanitary mask will be rendered unusable, thereby leaving an individual without a protective face mask in a time of need.

Therefore, there exists a long felt need in the art for a mask or PPE holding device which enables a mask wearer to easily store their mask on the device when not in use. There is also a long felt need in the art for a mask holder or support that is portable and that can be easily carried by an individual for use at different locations. Moreover, there is also a long felt need in the art for a mask holder that eliminates the need to keep the mask in or on an unsanitary and potentially infected surface, such as a pocket, table, etc., while the mask is not in use, and that is capable of supporting a plurality of different masks in an easily identifiable manner. Additionally, there is a long felt need in the art for a face mask holder that enables individuals to easily store their masks without the fear of the same becoming stolen, and that simultaneously sanitizes the mask during storage. Furthermore, there is a long felt need in the art for a mask-holding device that enables a shopkeeper or retail store location to conveniently display face masks and other personal protective equipment for sale to customers. Finally, there is a long felt need in the art for a mask-holding or supporting device that is relatively inexpensive to manufacture and both safe and easy to use.

The subject matter disclosed and claimed herein, in one embodiment thereof, comprises a mask display and storage stand in the form of a tree for hanging and displaying face masks, other PPE, accessories, and the like. The tree-like structure comprises a relatively flat base, a central supporting pole extending upwardly from the base, and a head which is removably attached to the flat base stand at the bottom end and removably attached to the head at the top end. A plurality of pegs or pins are also removably attached to the pole, wherein each peg or pin extends radially outward from the central supporting pole. Each peg has a terminal end with a vertical holder to hang the facemasks or accessories and prevent them from slipping off the pole. In further embodiments of the invention, the stand may further comprise one or more means of sanitizing the face masks stored on the stand.

In this manner, the novel mask or PPE support tree of the present invention accomplishes all of the forgoing objectives, and provides a relatively safe, sanitary and convenient solution to storing face masks and other personal protective equipment when the same are not in use. The mask tree of the present invention is also user-friendly, as it allows users to store multiple masks and other personal protective equipment as per the desires of the users and in an easily identifiable manner. Additionally, the mask tree unit is portable and can be easily carried by the user to various destinations, such as restaurants, bars, schools, churches and the like, and is also capable of sanitizing the masks stored thereon. The mask tree of the present invention eliminates the need to keep masks and other PPE in or on unsanitary places or surfaces, and ensures that the stored masks remain sanitary for use.

SUMMARY OF THE INVENTION

The following presents a simplified summary in order to provide a basic understanding of some aspects of the disclosed innovation. This summary is not an extensive overview, and it is not intended to identify key/critical elements or to delineate the scope thereof. Its sole purpose is to present some general concepts in a simplified form as a prelude to the more detailed description that is presented later.

The subject matter disclosed and claimed herein, in one embodiment thereof, comprises a mask display and storage stand in the form of a tree or other branched support to hang and display face masks, accessories or PPE. The support tree comprises a flat base stand, a pole centrally disposed on a top surface of the stand and a head. The pole is removably attached to the flat base stand at a bottom end of the pole, and is removably attached to the head at the top end of the pole. A plurality of pegs, dowels, pins or the like are removably attached to the pole along its length. Each peg extends radially outwardly from the pole, and each peg has one or more generally vertical holders at its terminal end, opposite to the end inserted into the center pole to hang or otherwise support the face masks, PPE or accessories.

In a further embodiment of the present invention, a one-piece mask tree is provided in order to hang and store face masks and PPE when not in use. The mask support includes a cylindrical pole that is integrally formed with a relatively flat base stand at its bottom end and has a geometrically shaped element, such as an oval, square or rectangular head positioned at its top end. A plurality of pegs extend outwardly from the side or exterior surface of the pole along its length and in different directions. The pegs are preferably similar in size and shape, but not orientation, such that no two pegs share the same vertical plane. Each of said pegs has at least two vertical holders at its terminal end to support and hang a face mask, PPE, accessory, etc.

In yet a further embodiment of the present invention, a mask display and/or storage tree is disclosed. The tree comprises an elongated pole removably attached to a flat base stand and a top head portion. One or more pegs are removably attached to the exterior surface or to each of the four open faces of the pole where the pole is of a rectangular configuration. Each peg has at least one vertical holder extending upwardly from the peg to hold and hang a face mask or an accessory. An electric motor is placed in or attached to the flat base stand and is configured to rotate the pole. The electric motor may also be used to drive a pump to disperse a sanitizing solution or mist to sanitize the face masks and other PPE when supported from the stand. The motor may be powered by batteries disposed in the base, or alternatively the stand may be plugged into an available outlet.

In yet a further embodiment of the present invention, a mask display and/or storage tree is disclosed. The tree stand comprises an elongated pole removably attached to a flat base stand and a top head portion. One or more pegs are removably attached to the exterior surface of the pole and extends outwardly therefrom. Each peg has at least one vertical holder extending upwardly from the peg to hold and hang a face mask or an accessory. The tree stand may further comprise a UV light near one or more of the pegs or from the top for use in sanitizing the face masks and other PPE supported by the pegs. The UV light source may be powered by batteries disposed in the base, or alternatively the tree stand may be plugged into an available outlet.

In still a further embodiment of the present invention, a method for assembling a display tree to support face masks and other PPE is disclosed. The method comprises the steps of connecting an elongated pole to a relatively flat base stand using a bolt, screw or other fastener mechanism at the end of the pole. The pole may also be placed into a clearance hole that is present at the center of the flat base stand. Next, one or more pegs or extenders are attached or inserted into the slots on the pole using an interlocking mechanism, such as male and female connectors. The head is then placed on the top of the pole and individual facemasks and/or accessories are hung on vertical holders present on the attached pegs or extenders for display or storage.

In one embodiment, the mask tree, display stand or storage stand is powered electrically using batteries or a power cord connected to the electric motor present within the flat base stand. The mask tree or display stand comes in multiple variants of a single unit or a version which can be assembled or disassembled. The mask tree can be used as a storage space for face masks and other PPE when not in use, or when the same require sanitizing. Ideally, the face masks or other PPE are spaced a distance sufficient from the central pole such that the same do not touch any dirty or contaminated surface and are suspended sufficiently above the surface upon which the base plate is placed.

The mask tree can be available commercially in various sizes, colors and materials with and/or without a rotating pole and/or sanitizing means (i.e., mist spraying, UV light, etc.). Individual components, such as pegs, the top portion or the flat base, can be purchased separately so that an individual can customize his or her stand to meet their personal preferences, and the various pegs can be color-coded to ensure that each user knows exactly which face mask and/or PPE stored on the stand belongs to them. There may also be a carrying pouch or pack for the tree to facilitate easy transportation when a user desires to transport the tree from one destination to the next.

To the accomplishment of the foregoing and related ends, certain illustrative aspects of the disclosed innovation are described herein in connection with the following description and the annexed drawings. These aspects are indicative, however, of but a few of the various ways in which the principles disclosed herein can be employed and are intended to include all such aspects and their equivalents. Other advantages and novel features will become apparent from the following detailed description when considered in conjunction with the drawings.

BRIEF DESCRIPTION OF THE DRAWINGS

The description refers to provided drawings in which similar reference characters refer to similar parts throughout the different views, and in which.

DETAILED DESCRIPTION OF THE INVENTION

Figure 1:
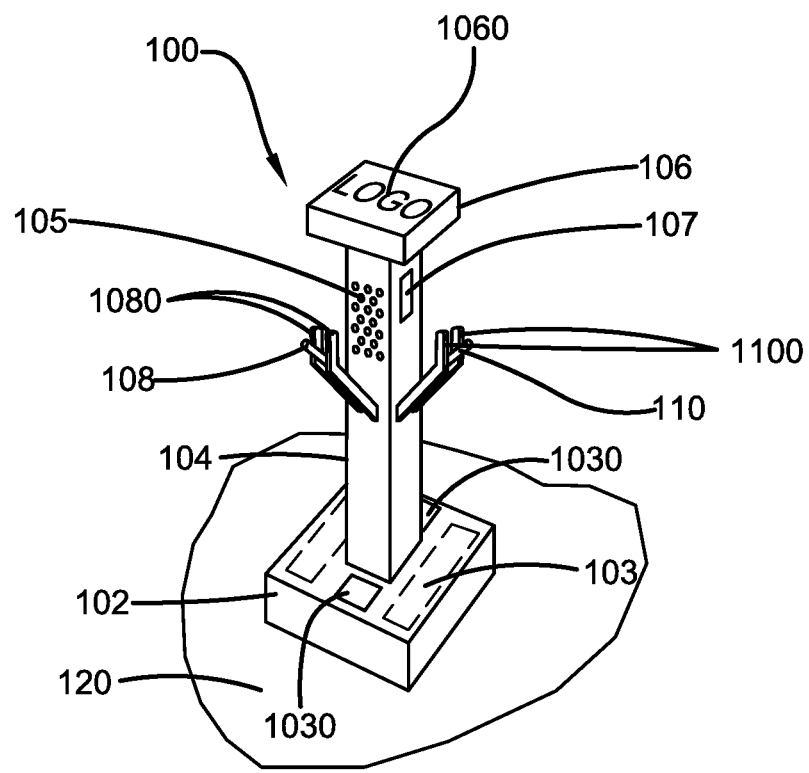
FIG. 1 illustrates a perspective view of one potential embodiment of the mask or PPE hanging stand of the present invention in accordance with the disclosed architecture.

The innovation is now described with reference to the drawings, wherein like reference numerals are used to refer to like elements throughout. In the following description, for purposes of explanation, numerous specific details are set forth in order to provide a thorough understanding thereof. It may be evident, however, that the innovation can be practiced without these specific details. In other instances, well-known structures and devices are shown in block diagram form in order to facilitate a description thereof. Various embodiments are discussed hereinafter. It should be noted that the figures are described only to facilitate the description of the embodiments. They are not intended as an exhaustive description of the invention and do not limit the scope of the invention. Additionally, an illustrated embodiment need not have all the aspects or advantages shown. Thus, in other embodiments, any of the features described herein from different embodiments may be combined.

As noted above, there is a long felt need in the art for a mask or PPE holding device that enables an individual to easily store their face mask on the device when not in use, and that can be conveniently carried by the individual to various locations as needed. There is also a long felt need in the art for a mask holder that eliminates the need to keep the mask on an unsanitary and potentially infected surface when not in use, and that is capable of supporting a plurality of different masks in an easily identifiable manner (i.e., so the masks of various individuals do not become commingled). Additionally, there is a long felt need in the art for a face mask holder that enables individuals to easily store their masks without the fear of the same becoming stolen, and that sanitizes the mask while the same is being stored thereon. Furthermore, there is a long felt need in the art for a mask holding device which enables a shopkeeper or retail store location to conveniently display face masks and other personal protective equipment for sale to customers. Finally, there is a long felt need in the art for a mask holding or supporting device that is relatively inexpensive to manufacture and both safe and easy to use.

Referring initially to the drawings, FIG. 1 illustrates a perspective view of one potential embodiment of the mask or PPE hanging stand 100 of the present invention in accordance with the disclosed architecture. In the present embodiment, the mask hanging stand 100 is in the form of a tree with a base 102, which is placed on a floor or other generally horizontal surface 120. A pole 104 of a desired height is connected or otherwise fastened to the base 102, and has one or more pegs 108, 110 positioned along its length or height for hanging masks, caps or any other similar lightweight accessory or jewelry items. The base 102 may further include a magnet or weights 103 (shown in phantom) for attaching the stand 100 to a metal surface. Alternatively, the base 102 may have suction cups (not shown) so that the tree can be better secured to a surface. The base 102 may also be weighted to prevent the base 102 from tipping over when a number of items are being supported by the pegs 108, 110 of the support pole 104.

As also shown in FIG. 1, the mask hanging stand 100 may further comprise a head or top element 106 that is attached to a distal end of the support pole 104, opposite the base 102. The head 106 may have a logo or trademark 1060 thereon for promotional purposes. Each peg or extender 108, 110 may further comprise one or more vertical holders. For example, peg 108 has a vertical holder 1080 and peg 110 has a vertical holder 1100, wherein ach of the vertical holders 1080, 1100 can be used to support a face mask, caps, PPE, jewelry or any other similar lightweight accessory or item and prevent the item from falling off the peg or extender 108, 110. Further, each of the pegs/extenders 108, 110 are preferably spaced apart from one another along the support pole, both laterally and vertically, such that no two pegs/extenders share the same vertical plane and the various items supported thereby do not contact one another. The pegs/extenders 108, 110 may also be color coded or bear other unique indicia so that they can be assigned to different individuals in an effort to avoid the face mask and other PPE of the various individuals using the mask stand 100 from becoming commingled.

The head portion 106 may be of any geometric or non-geometric configuration or take on an animate or other whimsical configuration. In one embodiment, the head 106 is shown as square or rectangular in shape and the pole 104 is substantially cuboidal in shape. As noted above, each side of the pole 104 can have one or more pegs 108, 110 to increase the capacity of the mask hanging stand 100. The stand 100 is solid and durable, yet relatively lightweight and easy to transport. The stand 100 may be presented for use as a single integrated unit, or may be in the form of a kit where the assembly and disassembly is easily done in seconds using a screw in the base 102 and the head 106.

The pegs 108, 110 can also be removably attached to the pole 104, and may be removed for transportation and easy storage. The pegs 108, 110 may also have a removable interlocking mechanism with the pole 104, which can be used to remove and attach the pegs. The pole 104 is also provided with vents or openings 105 which may be used to dispense a hydrogen peroxide or other solution to sanitize the masks or PPE that are supported by the tree 100. The sanitizing solution may be contained in a reservoir 1030 contained in the base 102 of the tree 100 that is in fluid communication with the openings 105. The mask tree 100 may also comprise one or more UV lights 107, which can be used to disinfect the face masks, PPE and other items being supported by the tree 100 when not in use, as explained more fully below.

Figure 2:
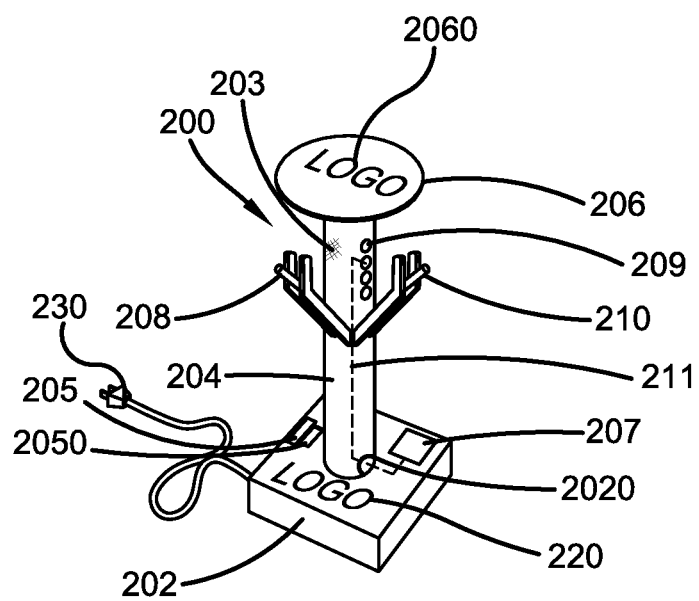
FIG. 2 illustrates a perspective view of one potential alternative embodiment of the mask or PPE hanging stand of the present invention in accordance with the disclosed architecture.

FIG. 2 illustrates a perspective view of one potential alternative embodiment of the mask or PPE hanging stand 200 of the present invention in accordance with the disclosed architecture. In this particular embodiment, the mask stand 200 has a generally circular head portion 206 connected to the distal end of the support pole 204. The head 2060 may have a logo, trademark, design or print 2060 for promotional purpose as per the desires of the users. Similarly, the same or a different logo 220 may be present on the base 202, which is attached to the proximal end of the support pole 204.

The shape of the base 202 can be any geometric configuration, such as a square, circle or oval as shown in the present embodiment. However, the shape and size of the base 202 and head 206 are not so limited and can be of other shapes and sizes to satisfy user need and/or preference. The pegs 208, 210 are removably attached to the pole 204 using a removable interlocking mechanism, or may be permanently fixed to the pole 204. The removable pegs or pins 208, 210 make the mask tree 200 portable and allow a user to more easily store the mask tree 200 when not in use. In the present embodiment, the pole 204 can also be a substantially cylindrical structure with no longitudinal edges and a smooth outer surface. The base or bottom stand 202 should have enough heft or supplemental weights 103 attached thereto or incorporated therein to firmly hold the pole 204, pegs 208, 210, and the masks or other protective personal equipment stored/hung on the pegs 208, 210 in an upright manner. The mask tree 200 may also be comprised of an antimicrobial material or coating 203, such as MicroBan®, to help in eliminating bacteria, viruses and other pathogens from the surface thereof.

The vertical holders present on the pegs 208, 210 of the mask stand 200 of the present invention extend vertically upward or outwardly from the end or near the end of each of the pegs 208, 210, and are substantially parallel to one another. The vertical holders 1080, 1100 may be integrally formed with, or removably attached to, the pegs 208, 210, and are used to support masks, PPE or other accessory items in a segregated and easily distinguishable manner.

Additionally, the upper or top surface of the base 202 of the mask stand 200 has an opening 2020 into which a bolt or screw present at the proximal end of the pole 204 is screwed into to form an interlocking mechanism. The male threads of the bolt or screw are locked with the female threads of the clearance opening 2020 for a stable and strong attachment between the base 202 and the pole 204. A similar locking mechanism can be used for connecting the head 206 and the pole 204 of the mask stand 200 of the present invention.

The opening 2020 is a cut-out portion at the center of the upper surface of the base 202 into which the bolt or screw or other fastening configuration is fixed. For example, instead of a threaded fastening system, a snap-locking system may be used. The pitch (distance) between adjoining threads of the bolt or screw and of the clearance opening 2020 should be similar for a safe and strong attachment. In yet another embodiment, the mechanism for interconnection between the pole 204 and each of the base 202 and the head 206 of the mask stand 200 can be one or more flange bolts.

In one variation of the present embodiment, the pole 204 of the mask stand 200 is rotatable in opening 2020, and an electric motor 205 may be fixed at the base 202 of the mask stand 200 to rotate the pole 204 about its longitudinal axis or centerline. The electric motor 205 is connected to the pole 204 and rotates the pole 204 at a relatively slow speed (e.g., 10-30 revolutions per minute) which enables each of the masks and other items supported by the pegs 108, 110 to pass by the UV light 107 or sanitizing mister as elsewhere described herein. To power the electric motor 205, an AC supply using a power cord 230 is provided. Alternatively, a built-in disposable or rechargeable battery 2050 can be used to provide power to the mask stand 200 and its various components. The motor 205 may also be used to drive a pump 207 to dispense the sanitizing solution out of the openings 209 positioned along the pole 204 that are in fluid communication with the reservoir 1030. More specifically, the sanitizing solution is channeled through the openings 209 via a line 211 in fluid communication with the reservoir 1030.

Figure 3:
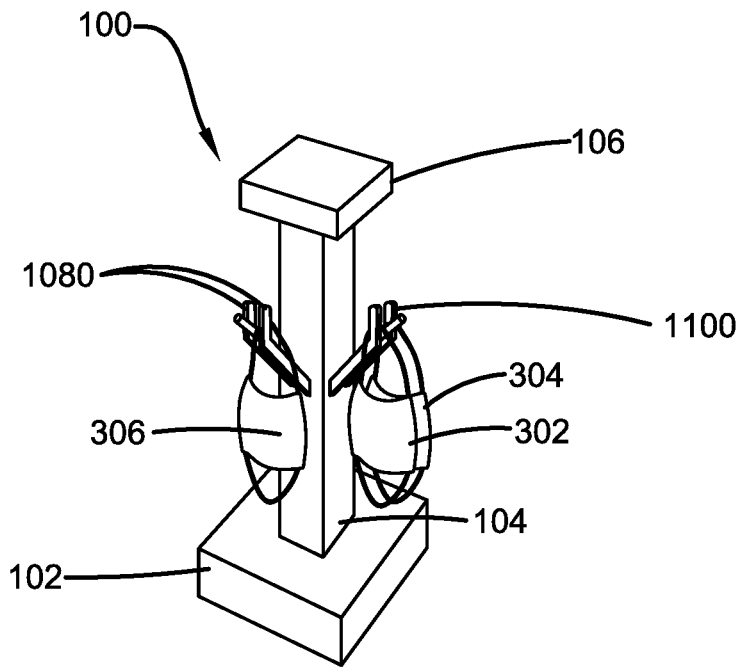
FIG. 3 illustrates a perspective view of one potential embodiment of the mask or PPE hanging stand of the present invention in accordance with the disclosed architecture, wherein the mask stand is being used to support a plurality of face masks.

FIG. 3 illustrates a perspective view of one potential embodiment of the mask or PPE hanging stand 100 of the present invention in accordance with the disclosed architecture, wherein the mask stand 100 is being used to support a plurality of face masks 302, 304, 306. As shown, any accessory, such as facemasks 302, 304, may be hung on the peg, pins or other extenders 110 using the holders 1100, and another accessory or facemask 306 may be hung on the peg 108 using the holder 1080 of the mask tree 100. In this manner, individual facemasks 302, 304, 306 may also be easily and distinctly displayed to a customer by a merchant without requiring a salesperson or employee to show an individual face mask to a customer.

Figure 4:
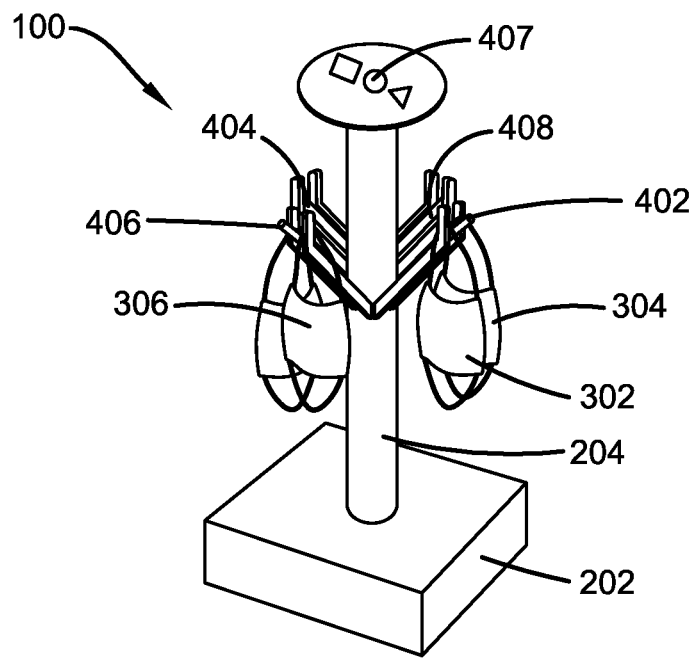
FIG. 4 illustrates a perspective view of one potential alternative embodiment of the mask or PPE hanging stand of the present invention in accordance with the disclosed architecture, wherein the mask stand is being used to support a plurality of face masks.

FIG. 4 illustrates a perspective view of one potential alternative embodiment of the mask or PPE hanging stand 100 of the present invention in accordance with the disclosed architecture, wherein the mask stand 100 is being used to support a plurality of face masks 302, 304, 306. The present embodiment has pegs 402, 404, 406, 408 present on each side of the pole or central stand 204 with multiple holders to hold the accessories 302, 304, 306. The vertical holders are present on each peg 402, 404, 406, 408 at different orientations to hold the various accessories apart from one another. It should be appreciated that any variation described earlier such as rotatable pole, fixed pole, single unit mask stand or modular mask stand can also be envisioned in the present embodiment as per the preferences of the user. The mask stand 100 may also be provided with a carrying pouch or pack for the stand to facilitate easy transportation and storage when not in use.

Figure 5:
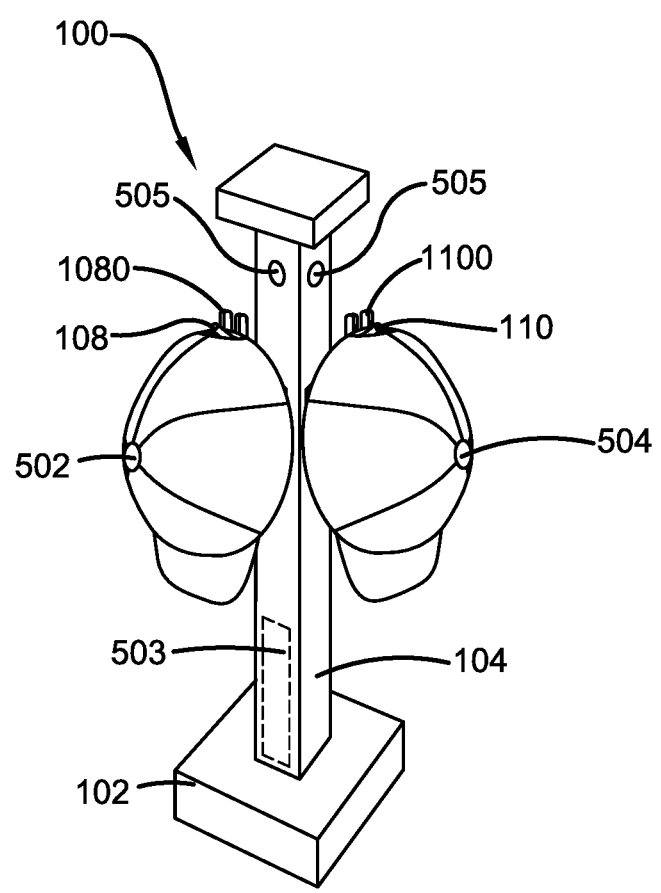
FIG. 5 illustrates a perspective view of one potential embodiment of the mask or PPE hanging stand of the present invention in accordance with the disclosed architecture, wherein the mask stand is being used to support a plurality of ball caps.

FIG. 5 illustrates a perspective view of one potential embodiment of the mask or PPE hanging stand 100 of the present invention in accordance with the disclosed architecture, wherein the mask stand 100 is being used to support a plurality of ball caps 502, 504. As shown, the pegs 108, 110 extend from the pole 104 and vertical holders 1080, 1100 extend from the pegs 108, 110 to support the caps 502, 504. In one embodiment, the stand 100 may support a power cord connected to a motor to rotate the pole 104 as per the requirement of a user as described above. In one variation of said embodiment, one or more LED lights 505 may also be present on the head, base and/or pegs to provide illumination to the display stand 100, and the base or pole may further comprise a storage area or cavity 503 (shown in phantom in FIG. 5) to store additional pegs.

The tree stands 100, 200 may include logos 1060, indicia, trademarks, geometric patterns, customizable colors and fonts, embroidery and prints and/or images 407 on their surface to alter the look of the stands 100, 200. Also, the tree stands 100, 200 may be constructed using any suitable and durable material such as, but not limited to plastic, metal, wood or other material. The tree stands 100, 200 can be placed on a table or other desired surface for people to hang their masks, PPE or other items, and the stands 100, 200 can be used in homes, bars, restaurants, schools and many other locations.

In one embodiment, the mask trees 100, 200 can be of a height ranging from one to three feet with two pegs connected to each face of the pole. Ideally, the first peg or pin should be a sufficient distance from the surface to allow a face mask to be hung from the pin without touching the surface on which the tree is supported, or at least 10 inches. In another embodiment, the mask trees 100, 200 can be of a height of approximately two feet with one peg connected to each face of the pole. For a floor stand, the mask tree 100, 200 can be of a height of approximately five feet with three pegs connected to each face of the pole. The number of vertical holders ranges in between two and five on each peg as per the preferred embodiment. Any other combination of sizes and numbers of pegs and holders are possible under any embodiment of the present invention. The mask tree 100, 200 can also come in various colors or be relatively transparent, and may be labeled with designated names, numbers, colors, identifiers, restaurant or business logos, team names, styles for each user's personal preference, etc. The tree can be used as an adjusted insert in car cupholder while driving.

Certain terms are used throughout the following description and claims to refer to particular features or components. As one skilled in the art will appreciate, different persons may refer to the same feature or component by different names. This document does not intend to distinguish between components or features that differ in name but not structure or function. As used herein "mask hanging stand", "mask display stand", "face mask tree", "mask holding stand", "mask stand", "accessory display stand", "mask holding device" and "mask holding unit" are interchangeable and refer to the face mask tree 100, 200 of the present invention.

Notwithstanding the forgoing, the face mask tree 100, 200 of the present invention can be of any suitable size and configuration as is known in the art without affecting the overall concept of the invention, provided that it accomplishes the above stated objectives. One of ordinary skill in the art will appreciate that the size, configuration and material of the face mask tree 100, 200 as shown in the FIGS. are for illustrative purposes only, and that many other sizes and shapes of the face mask tree 100, 200 are well within the scope of the present disclosure. Although the dimensions of the face mask tree 100, 200 are important design parameters for user convenience, the face mask tree 100, 200 may be of any size that ensures optimal performance during use and/or that suits the user's needs and/or preferences.

Various modifications and additions can be made to the exemplary embodiments discussed without departing from the scope of the present invention. While the embodiments described above refer to particular features, the scope of this invention also includes embodiments having different combinations of features and embodiments that do not include all of the described features. Accordingly, the scope of the present invention is intended to embrace all such alternatives, modifications, and variations as fall within the scope of the claims, together with all equivalents thereof.

What has been described above includes examples of the claimed subject matter. It is, of course, not possible to describe every conceivable combination of components or methodologies for purposes of describing the claimed subject matter, but one of ordinary skill in the art may recognize that many further combinations and permutations of the claimed subject matter are possible. Accordingly, the claimed subject matter is intended to embrace all such alterations, modifications and variations that fall within the spirit and scope of the appended claims. Furthermore, to the extent that the term "includes" is used in either the detailed description or the claims, such term is intended to be inclusive in a manner similar to the term "comprising" as "comprising" is interpreted when employed as a transitional word in a claim.

What is claimed is:

1. A PPE support tree comprising:
   a base having an opening;
   a pole having a first end and a second end, the first end sized and configured to fit within the opening;
   a top element disposed at the second end of the pole; and
   a plurality of pegs attached to the pole between the first and second ends, wherein each of the plurality of pegs comprise an upwardly extending element; and
   wherein the base comprises a magnet for securing the base to a surface and a first indicia disposed on the base; and
   wherein the top element comprises a second indicia disposed on the top element; and
   wherein the plurality of pegs are removably attached to the pole and oriented so that none of the plurality of pegs share a vertical plane; and an electric motor and a reservoir and a pump in communication with the electric motor, wherein the reservoir includes a supply of sanitizing solution.

2. The PPE support tree as recited in claim 1, wherein the base further comprises a suction cup to secure the base to a surface.

3. The PPE support tree as recited in claim 1, wherein the supply of sanitizing solution is hydrogen peroxide.

4. The PPE support tree as recited in claim 3, wherein the supply of sanitizing solution is dispensed out of an opening in the pole.

5. The PPE support tree as recited in claim 1 further comprising an anti-microbial agent integral with the PPE support tree.

6. The PPE support tree as recited in claim 1, wherein the electric motor rotates the pole about its longitudinal axis within the opening.

7. The PPE support tree as recited in claim 1 further comprising a UV light.

8. A face mask support comprising:
   a weighted base having an opening centrally disposed along a top surface of the weighted base;
   a pole having a first end and a second end, wherein the first end is positioned in the opening and extending outwardly therefrom; the pole comprising a plurality of openings wherein the plurality of openings are used for dispersing a sanitizing solution provided from a pump and a reservoir in the weighted base;
   a top affixed to the second end of the pole;
   a plurality of pegs extending outwardly from the pole; and
   an antimicrobial component; and
   wherein the base comprises a magnet for securing the base to a surface and a first indicia; and
   wherein the opening in the base is a cut-out in a center of an upper surface of the base; and
   wherein the first end of the pole screws into the opening in the base.

9. The face mask support as recited in claim 8, wherein the plurality of openings are for insertion of the plurality of pegs into the pole.

10. The face mask support as recited in claim 8 further comprising an electric motor for rotating the pole.

11. A sanitary face mask tree comprising:
    a central pole disposed in an opening in a base, the central pole having a top element secured to an end of the central pole opposite the base;
    a plurality of openings in the central pole;
    a plurality of pegs, wherein each of the plurality of pegs are into at least one of the plurality of openings in the central pole; and
    a sanitizing means, wherein the sanitizing means is at least one of a UV light and a sanitizing agent; and
    wherein each of the plurality of pegs comprises more than one vertical holder; and
    wherein the plurality of pegs are removably attached to the central pole and oriented so that none of the plurality of pegs share a vertical plane; and
    wherein the base comprises a supplemental weight to provide stability to the base.

* * * * *